United States Patent [19]
Miller et al.

[11] Patent Number: 5,336,156
[45] Date of Patent: Aug. 9, 1994

[54] INFANT INCUBATOR HUMIDIFIER

[75] Inventors: Kenneth G. Miller, Newport Beach, Calif.; James R. Grosholz, New Hope, Pa.

[73] Assignee: Air-Shields, Inc., Hatboro, Pa.

[21] Appl. No.: 762,653

[22] Filed: Sep. 19, 1991

Related U.S. Application Data

[63] Continuation of Ser. No. 499,093, Mar. 26, 1990, abandoned.

[51] Int. Cl.⁵ .................. A61G 11/00; A61M 15/00; A01K 41/00
[52] U.S. Cl. .................. 600/22; 128/203.17; 119/35; 119/41; 392/395; 392/403; 392/405
[58] Field of Search .................. 600/22; 392/394, 395, 392/402, 403, 405, 406, 394–395, 402–403, 405–406; 237/78 R, 78 A, 78 B; 261/D65, 139; 128/200.11, 203.16, 203.17; 219/401; 122/4 A, 13.2; 119/35–36, 41–43

[56] References Cited

U.S. PATENT DOCUMENTS

| | | | |
|---|---|---|---|
| 2,721,252 | 10/1955 | Dorsak | 219/38 |
| 3,806,102 | 4/1974 | Valenta et al. | 128/200.13 |
| 3,954,920 | 5/1976 | Heath | 261/104 |
| 3,982,095 | 9/1976 | Robinson | 128/200.11 |
| 4,133,302 | 1/1979 | McGrath et al. | 600/22 |
| 4,284,878 | 8/1981 | Bartels | 392/403 |
| 4,346,701 | 8/1982 | Richards | 128/200.14 |
| 4,529,867 | 7/1985 | Evelnosky | 219/274 |
| 4,563,313 | 1/1986 | Tsuaki | 261/81 |
| 4,652,408 | 3/1987 | Montgomery | 261/130 |
| 4,753,758 | 6/1988 | Miller | 261/139 |
| 4,796,605 | 1/1989 | Sasaki et al. | 600/22 |

FOREIGN PATENT DOCUMENTS 2173108 10/1986 United Kingdom .

*Primary Examiner*—Randall L. Green
*Assistant Examiner*—P. Zuttarelli
*Attorney, Agent, or Firm*—Ratner & Prestia

[57] ABSTRACT

An infant incubator humidifier having a heater within a heater tower which, in turn, is in heat transfer disposition with a metal sleeve mounted within a water reservoir through which air which is to be humidified is passed. The metal sleeve has a wick disposed on its outside surface and water in the reservoir is wicked along the wick, whereby air introduced into the reservoir is humidified upon contact with the wick.

27 Claims, 3 Drawing Sheets

INFANT INCUBATOR HUMIDIFIER

This application is a continuation of application Ser. No. 07/499,093, filed Mar. 26, 1990 abandoned.

TECHNICAL FIELD

The present invention relates, in general, to infant incubators and, in particular, to a humidifier for humidifying air supplied to an infant being maintained and treated in an infant incubator.

BACKGROUND OF THE INVENTION

As part of the maintenance and treatment of an infant in an incubator, the air supplied to the infant is humidified. Typically, infant incubators have built-in humidifiers through which filtered inlet air is passed. In addition, external humidifiers, which introduce filtered humidified air directly into the hood of the incubator, are available.

Various problems exist with currently available infant incubator humidifying apparatus. For incubators having built-in humidifiers, inlet air to the incubator is filtered before the air enters the circulation path which extends through the hood area in which an infant is maintained and treated. Typically, the filtered air is drawn by a fan in the circulation path and conducted into the hood through a first passage. The air leaves the hood through a second passage and is conducted back to the first passage for recirculation through the hood. A heater and a humidifier are located in the air circulation path, so that the air which is introduced into the hood has the proper temperature and humidity.

The hood of an infant incubator usually is arranged with arm ports and a door to permit access to the infant if the need arises to treat the infant or to position sensors, probes and the like on the infant. When personnel attending an infant open the hood door or place their arms through the arm ports, contaminants can be introduced from the hands of such personnel and, to a lesser extent, from the environment outside the incubator.

Many users of infant incubators have the perception that such contaminants, which become airborne and enter the air circulation path, are the origin of airborne bacteria formed in the reservoir of the humidifier as the air flow with the contaminants passes through the humidifier, whereby the infant is exposed to this bacteria. Although this perception has not been substantiated, many users who have this perception, nevertheless, do not make use of the humidifier, for example, leaving the reservoir empty. Instead, they employ external humidifiers which introduce filtered or unfiltered, humidified air directly into the hood of the incubator. If the incoming humidified air from an external humidifier is not filtered appropriately, this air can carry its own variety of airborne pathogens if the humidifier reservoir is not rigorously maintained.

Such external humidifiers have a number of shortcomings. First, they require a source of pressurized gas (oxygen, air or oxygen/air mixture) to force humidified air into the incubator hood. Second, provision must be made for passing through the hood tubing and conduits through which the humidified air is conducted into the hood. Third, the presence of such tubing and conduits can impede the maintenance and treatment of an infant within the hood. Fourth, tubing and conduits leading into the incubator hood have a propensity for a temperature drop across their lengths which can result in water vapor condensing back into a liquid state. Water in the tubing and conduits can be absorbed by linens in the incubator, thus increasing the possibility of bacteria colonization in both the tubing and conduits and the absorbent materials in the incubator. Fifth, external humidifiers generally are mounted on IV poles and the like which take up space in already crowded nurseries.

SUMMARY OF THE INVENTION

Accordingly, an infant incubator humidifier constructed in accordance with the present invention includes a water reservoir adapted to contain water and has means for passing air through the water reservoir. Also included are a tubular metal sleeve mounted within the water reservoir and a wick disposed on the outside surface of the metal sleeve. An infant incubator humidifier constructed in accordance with the present invention further includes a heater tower within the sleeve in heat transfer disposition with the inside surface of the metal sleeve in the water reservoir and a heater disposed within the heater tower.

In a preferred embodiment of the present invention, the humidifier is an "external" unit adapted for selective connection into and removal from an air flow path of an infant incubator. However, it will be apparent to those skilled in the art that the present invention has application as a humidifier permanently installed in an incubator.

DETAILED DESCRIPTION OF THE INVENTION

Figure 1:
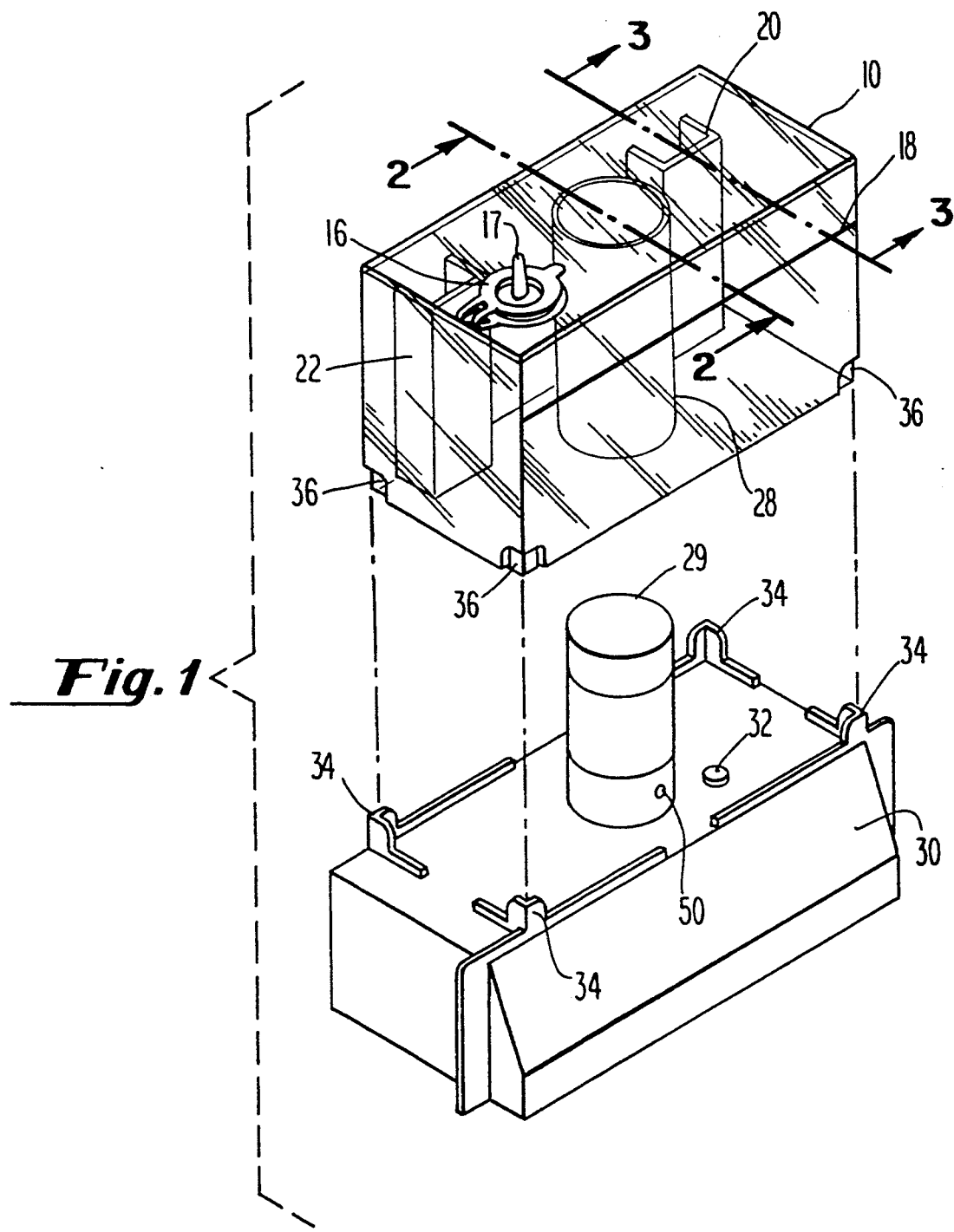
FIG. 1 is an exploded perspective view of an infant incubator humidifier constructed in accordance with the present invention.

Referring to the drawings, an infant incubator humidifier, constructed in accordance with the present invention, includes a water reservoir 10 having means for passing air through the water reservoir to humidify the air. Water reservoir 10 preferably is made of a transparent plastic material, so that the level of the water within the reservoir can be observed visually.

Air is introduced into water reservoir 10 through an inlet port 12 in a vertical wall 14 of the water reservoir and humidified air leaves the water reservoir through an outlet port 13 also in vertical wall 14. As will be explained hereinafter, the configuration of the inlet and outlet ports is selected to adapt the humidifier for selective connection to and removal from an infant incubator as described, illustrated and claimed in a copending application by Joseph J. Moffett and James R. Grosholz filed concurrently with this application assigned Ser. No. 07/499,091 and entitled "Infant Incubator." This copending application has been abandoned in favor of a continuation application filed Nov. 26, 1991 which has been assigned Ser. No. 07/799,711 and is incorporated by reference as if its drawings and text were fully included herein. However, it will be apparent to those skilled in the art that the present invention has application with other types of incubators.

Water is introduced into water reservoir 10 through a fill port 16 in the top of the water reservoir by lifting the cap of the fill port. Alternatively, water may be introduced from a sterile bag or bottle with an IV set connected to a nipple 17 formed as part of the cap of the fill port. Preferably, a line 18 is scored into water reservoir 10 to define a predetermined water-fill level.

For the particular embodiment of the present invention illustrated in the drawings, the inlet and outlet ports of water reservoir 10 are below water-fill line 18. In order to prevent water in water reservoir 10 from flowing out of the water reservoir, the water reservoir has a pair of standpipes 20 and 22 extending upward from the inlet and outlet ports, respectively, to a point above water-fill line 18. Each standpipe includes a tubular passage and a surface, identified by reference numeral 24 for standpipe 20, extending across the tubular passage from the associated port. In this way, inlet air, entering through inlet port 12, is directed upward through standpipe 20 and humidified outlet air is drawn downward through outlet port standpipe 22 and directed through the outlet port.

An infant incubator humidifier, constructed in accordance with the present invention, further includes a tubular metal sleeve 26 mounted within water reservoir 10 and a wick 28 disposed on the outside surface of sleeve 26. Sleeve 26 preferably is cylindrical and wick 28, made from an absorbent material such as paper or textile, preferably completely covers the outside surface of the sleeve. Water in water reservoir 10 is wicked upwardly to humidify inlet air, introduced through inlet port 12 and inlet port standpipe 20, as the inlet air contacts the wick.

An infant incubator humidifier, constructed in accordance with the present invention, also includes a heater tower 29 positioned within sleeve 26 in heat transfer disposition with the inside surface of the sleeve. With sleeve 26 cylindrical, heater tower 29 also is cylindrical.

As illustrated, heater tower 29 is mounted on a heater controller base 30 upon which water reservoir 10 rests. The various components are arranged, so that water reservoir 10 is movable relative to heater controller base 30 in a direction along the longitudinal axis of heater tower 29 by sliding the inside surface of sleeve 26 over the outside surface of the heater tower. This arrangement facilitates filling water reservoir 10 with water and cleaning or replacing the water reservoir.

To assure proper placement of the water reservoir 10 on heater controller base 30 before the humidifier can be operated, an interlock switch 32 is provided in the surface of the heater controller base upon which the water reservoir rests. Interlock switch 32 is engaged by the water reservoir as the water reservoir is mounted on the heater controller base to control the humidifier circuitry and permit operation of the humidifier. When water reservoir 10 is removed from heater controller base 30, heater 38 is disconnected from its source of power by interlock switch 32.

As seen most clearly in FIG. 1, heater controller base 30 has molded-in ribs 34 which are received in corresponding shaped recesses 36 in water reservoir 10. These ribs and recesses are provided to facilitate proper alignment of the water reservoir and the heater controller base and preclude relative rotation and misfitting.

An infant incubator humidifier, constructed in accordance with the present invention, also includes a heater 38 disposed within heater tower 29. For the embodiment of the present invention illustrated in the drawings, heater tower 29 is formed of three parts. Upper part 40 and lower part 42 preferably are formed of a plastic material, while intermediate part 44, within which heater 38 is disposed, preferably is formed of aluminum.

Figure 5:
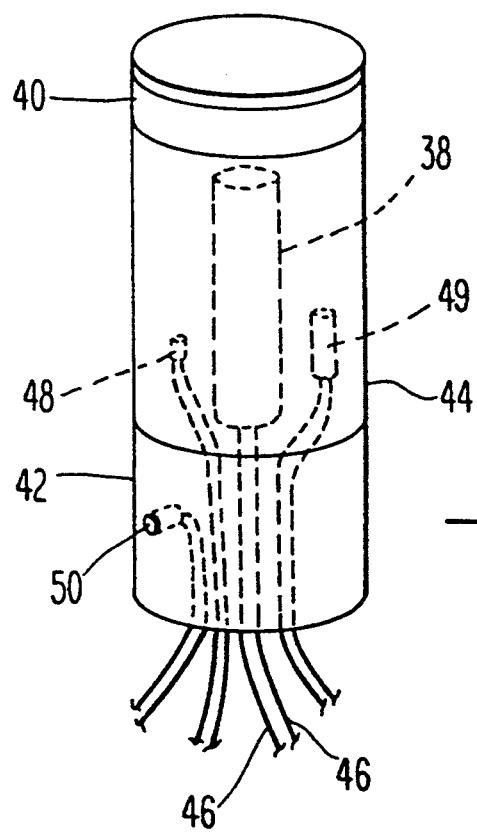
FIG. 5 is a perspective view, on an enlarged scale, of the heater tower of the FIG. 1 infant incubator humidifier showing the components within the heater tower.

Heater 38, preferably a cartridge heater of conventional construction and operating, is, as shown in FIG. 5, powered through a pair of leads 46. The heat generated by heater 38 is conducted by aluminum part 44 to tubular metal sleeve 26 in water reservoir 10 to heat the water in the reservoir, so that heated water is wicked upwardly by wick 28. Heater 38 also heats and maintains the temperature of the wick above the water level which assists in raising the temperature of the air passing through the humidifier to permit the air to hold a greater amount of liquid in the vapor phase Temperature control of heater 38 is achieved by a thermistor 48, positioned in aluminum part 44, and conventional circuitry which responds to the thermistor to regulate the power delivered to the heater. In this way, the water in water reservoir 10 can be heated to a desired temperature. The control circuitry also includes means for adjustment of the desired heater temperature.

Heater tower 29 preferably has a second thermistor 49 for sensing excessive temperatures. Circuitry of conventional design and operation, responsive to thermistor 49, will cut off the power delivered to heater 38 upon thermistor 49 sensing a temperature of aluminum part 44 which exceeds a prescribed level.

As indicated previously, with water reservoir 10 made of a transparent material, the water level within the water reservoir can be observed visually. According to a specific aspect of the present invention, a "low water" condition can be indicated automatically. This is accomplished by a third thermistor 50 fitted within an opening in the surface of heater tower 29 at a predetermined point. In particular, thermistor 50 is in plastic lower part 42 of the heater tower and is in heat transfer disposition with metal sleeve 26 in water reservoir 10. As the level of the water in the water reservoir drops below a predetermined level, the loss of cooling effect of the water is sensed by thermistor 50 and circuitry of conventional design and operation develops an indication of this condition which is displayed, for example, on heater controller base 30 or sounded by an audible alarm.

Figure 2:
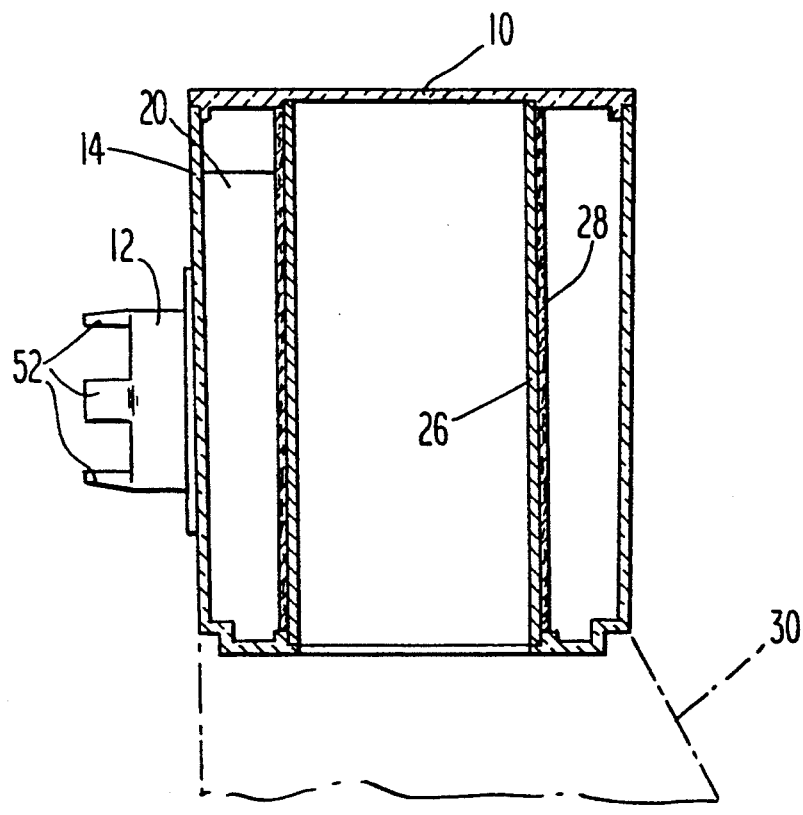
FIG. 2 is a sectional view taken along line 2—2 of FIG. 1.
Figure 3:
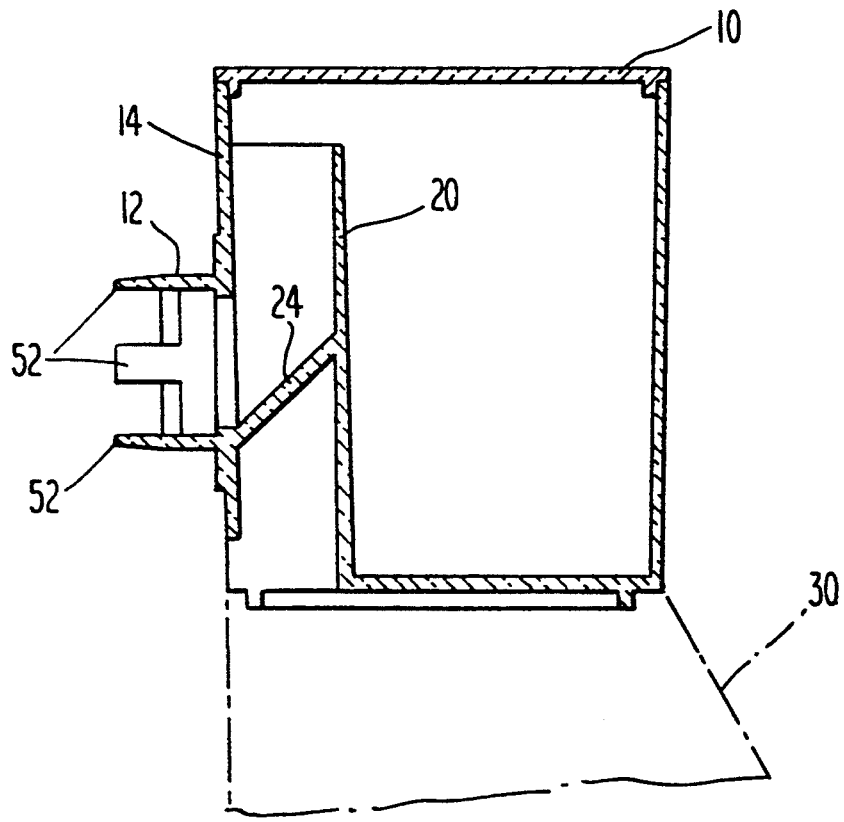
FIG. 3 is a sectional view taken along line 3—3 of FIG. 1.
Figure 4:
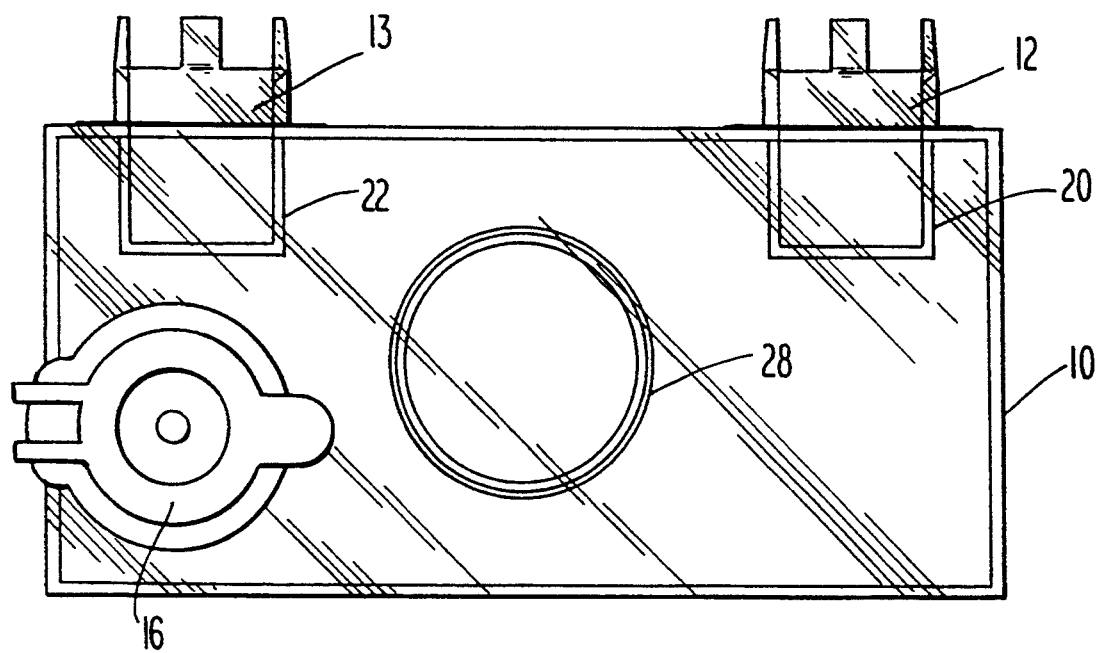
FIG. 4 is a top view of the FIG. 1 infant incubator humidifier.

The embodiment of the present invention illustrated in the drawings is particularly suited for use with certain types of infant incubators already in service. By arranging the air inlet line of an incubator with suitable valves, filtered inlet air can be diverted through the humidifier and humidified air can be introduced into the air circulation path of the incubator. The valves, arranged to be operated by the inlet port coupling and the outlet port coupling of the humidifier, selectively connect the humidifier to receive filtered inlet air and disconnect the humidifier. As shown in FIGS. 2 and 3, the inlet port coupling and the outlet port coupling each have a plurality of prongs 52, whereby air can pass through these couplings into the humidifier.

The foregoing has set forth an exemplary and preferred embodiment of the present invention. It will be understood, however, that various alternatives will occur to those of ordinary skill in the art without departure from the spirit and scope of the present invention.

What is claimed is:

1. An infant incubator humidifier comprising:
a heater controller base;
a heater tower mounted on said heater controller base and having a longitudinal axis;
a water reservoir having a top and unattached to said heater controller base and movable relative to said heater controller base in a direction along said longitudinal axis of said heater tower to and from a position in which said water reservoir rests upon said heater controller base, said water reservoir adapted to contain water and having:
   (a) air inlet means opening into said water reservoir only near said top of said water reservoir for introducing inlet air into said water reservoir, and
   (b) air outlet means opening into said water reservoir only near said top of said water reservoir for conducting humidified air from said water reservoir;
a tubular metal sleeve mounted within said water reservoir and within which said heater tower is positioned, said sleeve having an outside surface and inside surface in heat transfer disposition with said heater tower when said water reservoir rests on said heater controller base;
a wick disposed on said outside surface of said sleeve;
a heater disposed within said heater tower;
and alignment means for preventing relative rotation between said heater controller base and said water reservoir about said longitudinal axis of said heater tower when said water reservoir rests upon said heater controller base.

2. An infant incubator humidifier according to claim 1 wherein said alignment means include a plurality of ribs on said heater controller base and a plurality of recesses in said water reservoir in which said ribs are received when said water reservoir rests upon said heater controller base.

3. An infant incubator humidifier comprising:
a heater controller base;
a heater tower mounted on said heater controller base and having a longitudinal axis;
a water reservoir having a top and movable relative to said heater controller base in a direction along said longitudinal axis of said heater tower to and from a position in which said water reservoir rests upon said heater controller base, said water reservoir adapted to contain water and having:
   (a) a vertical wall,
   (b) air inlet means extending through said vertical wall and opening into said water reservoir only near the top of said water reservoir for introducing inlet air into said water reservoir, and
   (c) air outlet means extending through said vertical wall and opening into said water reservoir only near the top of said water reservoir for conducting humidified air from said water reservoir;
a tubular metal sleeve mounted within said water reservoir and within which said heater tower is positioned, said sleeve having an outside surface and inside surface in heat transfer disposition with said heater tower when said water reservoir rests on said heater controller base;
a wick disposed on said outside surface of said sleeve;
a heater disposed within said heater tower;
and alignment means for preventing relative rotation between said heater controller base and said water reservoir about said longitudinal axis of said heater tower when said water reservoir rests upon said heater controller base.

4. An infant incubator humidifier according to claim 3 wherein said alignment means include a plurality of ribs on said heater controller base and a plurality of recesses in said water reservoir in which said ribs are received when said water reservoir rests upon said heater controller base.

5. An infant incubator humidifier comprising:
a heater controller base;
a heater tower mounted on said heater controller base and having a longitudinal axis;
a water reservoir having a top and movable relative to said heater controller base in a direction along said longitudinal axis of said heater tower to and from a position in which said water reservoir rests upon said heater controller base, said water reservoir adapted to contain water and having:
   (a) air inlet means opening into said water reservoir near the top of said water reservoir for introducing inlet air into said water reservoir, and
   (b) air outlet means opening into said water reservoir near the top of said water reservoir for conducting humidified air from said water reservoir;
a tubular metal sleeve mounted within said water reservoir and within which said heater tower is positioned, said sleeve having and outside surface and an inside surface in heat transfer disposition with said heater tower when said water reservoir rests on said heater controller base;
a wick disposed on said outside surface of said sleeve;
a heater disposed within said heater tower;
and an electrical interlock switch positioned in a surface of said heater controller base upon which said water reservoir rests and which is engaged by said water reservoir when said water reservoir rests on said heater controller base to control power supplied to said heater.

6. An infant incubator humidifier according to claim 5 wherein said water reservoir is formed of transparent material.

7. An infant incubator humidifier according to claim 5 wherein said water reservoir has a fill port in said top of said water reservoir through which water is introduced into said water reservoir.

8. An infant incubator humidifier according to claim 5 further including means within said heater tower for sensing the level of water in said water reservoir.

9. An infant incubator humidifier according to claim 5 wherein said plurality of sidewalls, said floor and said top of said water reservoir are a preformed unitary unit.

10. An infant incubator humidifier according to claim 5 wherein said sleeve and said heater tower are cylindrical.

11. An infant incubator humidifier according to claim 10 wherein said wick is an absorbent material which completely covers said outside surface of said sleeve.

12. An infant incubator humidifier according to claim 5 wherein said water reservoir has a plurality of sidewalls and a floor, said air inlet means include an inlet port in one of said sidewalls of said water reservoir through which inlet air enters said water reservoir and an inlet standpipe extending upward from said inlet port to a point above a predetermined water-fill level and through which inlet air passes, and said air outlet means include an outlet port in one of said sidewalls of said water reservoir through which humidified air leaves said water reservoir and an outlet standpipe extending upward from said outlet port to a point above said predetermined water-fill level and through which humidified air passes.

13. An infant incubator humidifier according to claim 12 wherein:
   (a) said inlet standpipe includes a vertically disposed first tubular passage and a surface extending across said first tubular passage from said inlet port, and
   (b) said outlet standpipe includes a vertically disposed second tubular passage and a surface extending across said second tubular passage from said outlet port.

14. An infant incubator humidifier according to claim 5 further including means for selectively inserting said humidifier into an air passage of an incubator and removing said humidifier from an air passage of an incubator.

15. An infant incubator humidifier according to claim 14 wherein said water reservoir is formed of transparent material.

16. An infant incubator humidifier according to claim 14 wherein said wick is an absorbent material which completely covers said outside surface of said sleeve.

17. An infant incubator humidifier according to claim 14 wherein said water reservoir has a fill port in said top of said water reservoir through which water is introduced into said water reservoir.

18. An infant incubator humidifier according to claim 14 further including means within said heater tower for sensing the level of water in said water reservoir.

19. An infant incubator humidifier according to claim 14 wherein said plurality of sidewalls, said floor and said top of said water reservoir are a preformed unitary unit.

20. An infant incubator humidifier according to claim 14 wherein said means for selectively inserting and removing said humidifier include first and second couplings projecting from an outside surface of said water reservoir and adapted to actuate first and second valves in said air passage of said incubator.

21. An infant incubator humidifier according to claim 14 wherein said air inlet means include an inlet port in a sidewall of said water reservoir through which inlet air enters said water reservoir and said air outlet means including an outlet port in said sidewall of said water reservoir through which humidified air leaves said water reservoir.

22. An infant incubator humidifier according to claim 21 wherein each of said inlet port and said outlet port include a coupling projecting from said sidewall of said water reservoir and adapted to actuate a valve in said air passage of said incubator.

23. An infant incubator humidifier according to claim 14 further including alignment means for preventing relative rotation between said heater controller base and said water reservoir about said longitudinal axis of said heater tower when said water reservoir rests upon said heater controller base.

24. An infant incubator humidifier according to claim 14 wherein said sleeve and said heater tower are cylindrical.

25. An infant incubator humidifier according to claim 23 wherein said alignment means include a plurality of ribs on said heater controller base and a plurality of recesses in said water reservoir in which said ribs are received when said water reservoir rests upon said heater controller base.

26. An infant incubator humidifier according to claim 14 wherein said water reservoir has a plurality of sidewalls and a floor, said air inlet means include an inlet port in one of said sidewalls of said water reservoir through which inlet air enters aid water reservoir and an inlet standpipe extending upward from said inlet port to a point above a predetermined water-fill level and through which inlet air passes, and said air outlet means include an outlet port in one of said sidewalls of said water reservoir through which humidified air leaves said water reservoir and an outlet standpipe extending upward from said outlet port to a point above said predetermined water-fill level and through which humidified air passes.

27. An infant incubator humidifier according to claim 26 wherein:
   (a) said inlet standpipe includes a vertically disposed first tubular passage and a surface extending across said first tubular passage from said inlet port, and
   (b) said outlet standpipe includes a vertically disposed second tubular passage and a surface extending across said second tubular passage from said outlet port.

* * * * *